United States Patent [19]  [11] 4,049,427
Guerra  [45] Sept. 20, 1977

[54] NON-PRECIOUS DENTAL ALLOY

[76] Inventor: Ricardo Guerra, 112 Bellevue Ave., Oceanside, N.Y. 11572

[21] Appl. No.: 730,704

[22] Filed: Oct. 8, 1976

[51] Int. Cl.² .............................................. C22C 19/05
[52] U.S. Cl. ...................................................... 75/171
[58] Field of Search .................... 75/171, 170; 148/32, 148/32.5

[56] References Cited

U.S. PATENT DOCUMENTS 3,749,570  7/1973  Lyon ....................................... 75/171

*Primary Examiner*—R. Dean
*Attorney, Agent, or Firm*—Bauer, Amer & King

[57] ABSTRACT

A non-precious dental alloy is disclosed which is particularly useful in dental prosthesis, is strong, oxidation-resistant, aesthetically pleasing and compatible with porcelain bonding upon being formed into complicated shapes. The alloy consists of, by weight, 14–21% Cr, 0.9–1.4% Be, 0.3–0.4% Cu, 8–12% Co, 0.03–0.05% Mn, 0.8–1.2% Fe, 1–1.5% Mo, 1–1.5% Al, 0.3–0.4% Si, balance Ni.

3 Claims, No Drawings

NON-PRECIOUS DENTAL ALLOY

BACKGROUND OF THE INVENTION

The present invention relates to dental alloys and, particularly, to non-precious dental alloys for use with procelain veneers in the manufacture of dentures, dental bridges and the like.

Metal alloys for dental prosthesis were, in the past, based on gold and/or silver, particularly on gold. The high cost of gold, however, due to its natural scarcity and competing uses in the field of jewelry has unnecessarily exaggerated the cost of gold-based dental prosthetic devices. In addition, the low tensile strength of gold makes this metal not entirely satisfactory in many respects. Further, although gold accepts readily a porcelain coating, it frequently requires a separate bonding layer because its natural oxide layer is not adequate in all respect for bonding porcelain.

A non-precious alloy which has been believed suitable for dental work, is described in the U.S. Pat. No. 3,459,545 as an alloy for turbine blades in gas turbine engines. However, it contains 1.8–3% tungsten, 0.5–2% columbium, 1–3% tantalum, 3–4% titanium and, as such, besides being rather expensive, it possesses an unduly high Brinnell hardness value, which makes the preparation and the finishing of the dental work exceedingly harduous. The melting point of this alloy is also unnecessarily considerably higher than that of a gold alloy.

Other known compositions, primarily based on nickel, include berryllium as a critical alloying element. Such alloys as those described in U.S. Pat. No. 3,749,570 have been criticized recently in that problems are encountered both in the preparation of the alloy and in the preparation of prosthetic devices because of the rather toxic nature of beryllium. The prior art has shunned these alloys as hazardous. However, from "An evaluation of non-precious alloys for use with procelain veneers — part II — industrial safety and biocompatibility", a study made by Drs. Moffa, Guckes, Okawa and Lilly of the U.S. Public Health Service Hospital, San Francisco, Calif. (The Journal of Prosthetic Dentistry, St. Louis, vol. 30, no. 4, part I, pp. 432–441, October 1973) it results that, to date, there have been no documented cases of beryllium toxicity of dental origin and that any dangers of toxicity are limited to certain operations in the preparation of dental prosthetic devices. Several Be-containing alloys have been tested, such as those sold under the trade names Vera Bond, Wiron, Gemini II, etc. but no detectable amount of Be concentration was found even during grinding — the most prone operation to toxic environment — and polishing of dental prosthetic devices, provided that the obvious precautions of employing an adequate exhaust ventilation system were observed.

Other alloys known in the art contain no iron, because iron results generally in a blackening of the prosthetic device. An example of such alloy is offered by U.S. Pat. No. 3,896,547. However, it has been found that, when properly combined with other elements, iron will enhance the bonding of the alloy of the procelain veneer, while the lack of iron will invariably result in a poor bonding.

It is, therefore, an object of the present invention to overcome the disadvantages of the alloys of the prior art by providing a non-precious alloy which is resistant to oxidation, does not form black oxides, has a good coefficient of thermal expansion which is compatible with procelains, has a Brinnell hardness and a melting point comparable to gold-base alloys and is easy to grind.

DESCRIPTION OF THE INVENTION

Briefly stated, the alloy of the invention consists of, by weight: 14–21% Cr, 0.9–1.4% Be, 0.3–0.4% Cu, 8–12% Co, 0.03–0.05% Mn, 0.8–1.2% Fe, 1–1.5% Mo, 1–1.5% Al, 0.3–0.4% Si, balance Ni. This composition has been found not to be subject to oxidation when the various layers of porcelain are fired thereon. This is contrary to all known alloys for dental prosthesis, especially those containing iron, even in equivalent amount, because these alloys, when fired, form a black oxide which detracts from the aesthetic appearance of the finished article. The alloy of the invention form a yellowish oxide which blends very well in color with the porcelain layer and acrylic facings of the finished article.

Even without the introduction of such elements as Ti, W, Ta, Cb, a tensile strength of the order of 100,000 psi and an elongation of 8–16% is achieved by the alloy of the invention. Furthermore, a coefficient of thermal expansion is obtained which is very compatible with that of the porcelain jackets, thus obviating hairline cracks caused when contacting the dental finished work with hot and cold foods.

Copper, which is often absent in prior art alloys, is used in the present alloy to provide a pleasing coloration of the finished article and also to lower the Brinnell hardness and the melting point of the alloy to render it comparable with gold-based alloys. The Brinnell hardness of the alloy of the invention was found to be in the range of 190–210 and the melting point in the neighborhood of 2450° F.

The standard technique for the preparation of dental prosthetic devices is well known to the expert in the field. It involves the melting of the various elements, followed by the casting of the melt by investment in the proper mold. In making the melt of the present alloy, however, the molybdenum and the beryllium are added last. After casting, the dental device is trimmed and a so-called "gold conditioner" (a flux well known in the art) is applied to obtain a good bond to the procelain jacket applied to the trimmed casting.

While most prior art alloys are difficult to grind because of their high Brinnell value, generally around 350, the alloy of the present invention is easy to grind and, taken the necessary ventilation precautions mentioned hereabove, the presence of beryllium in the alloy will not constitute any undue health hazard, as found in the cited evaluation of Be-containing alloys. It has also been found that the investment casting cement will clean off readily from the alloy of the invention, similarly to gold alloys and contrary to other non-precious prior art alloys.

Compared with gold-base alloys, the alloy of the invention has been found to form considerably stronger margins which means that the margins may be made thinner, thus permitting the application of a thicker aesthetic facing. It has also been found that the alloy of the invention is suitably compatible with all types of porcelain available at present on the market and utilized in dental work.

As an illustration of the alloy of the invention, the following melt was prepared, by weight percent:

Nickel : 66.78

Chromium : 17.60
Cobalt : 9.99
Molybdenum : 1.36
Aluminum : 1.29
Beryllium : 1.19
Copper : 0.34
Silicon : 0.39
Iron : 1.02
Manganese : 0.04

The Molybdenum and the Beryllium were added last to the melt. The molten composition was then investment cast to form a denture and, upon cleaning off of the investment cement, it was trimmed and a "gold conditioner" was applied to form a good bonding with the porcelain jacket. Grinding, porcelain-firing, polishing and final touching completed the operation.

The finished product was found to have a pleasing coloration, no hairline cracks, no black-oxidation showing through the porcelain coating; it was found to be very easy to grind and to polish and to possess unusually strong margins thus allowing the application of thicker procelain veneers.

A portion of the melt was tested for its physical properties and was found to have the following characteristics:

tensile strength : 100,000 psi
elongation : 8–16%
Brinnell hardness : 190–210
specific gravity : 8
melting point : 2450° F Comparative tests, using known alloys, were conducted, adopting identical melting, casting and preparatory techniques. It was found that an alloy lacking iron resulted in a very poor bonding thereof to the procelain. A Microbond alloy was observed to create gas holes in the applied procelain facing. A Gemini II alloy was noted to allow blackening to show through the veneer of porcelain.

Additional tests were made altering the composition of the illustrated alloy within ± 20% of the composition given. It was found that within this range, the physical characteristics of the alloys and the resulting properties of the finished products did not change appreciably.

Although the present invention has been described with respect to a specific embodiment as illustrated, it is not limited thereto but it is intended to cover all modifications and equivalents evident to one skilled in the art without departing from the spirit of the invention.

What is claimed is:

1. An alloy suitable for dental prosthetic work consisting essentially of, by weight: 14–21% chromium, 8–12% cobalt, 1–1.5% molybdenum, 1–1.5% aluminum, 0.9–1.4% beryllium, 0.8– 1.2% iron, 0.3–0.4% copper, 0.3–0.4% silicon, 0.03–0.05% manganese, balance nickel.

2. The alloy according to claim 1, consisting of, by weight, about 66.8% Ni, 17.6% Cr, about 1.2% Be, about 0.3% Cu, about 10.0% Co, 0.04% Mn, about 1.0% Fe, about 1.4% Mo, about 1.3% Al, about 0.4% Si.

3. The alloy according to claim 1, consisting of, by weight, 66.78% Ni, 17.60% Cr, 1.19% Be, 0.34% Cu, 9.99% Co, 0.04% Mn, 1.02% Fe, 1.36% Mo, 1.29% Al, 0.39% Si.

* * * * *